(12) United States Patent
Kaul et al.

(10) Patent No.: US 8,435,798 B2
(45) Date of Patent: May 7, 2013

(54) APPLICATIONS AND METHODS OF OPERATING A THREE-DIMENSIONAL NANO-ELECTRO-MECHANICAL RESONATOR AND RELATED DEVICES

(75) Inventors: Anupama B. Kaul, Arcadia, CA (US); Larry W. Epp, Pasadena, CA (US); Leif Bagge, Austin, TX (US)

(73) Assignee: California Institute of Technology, Pasadena, CA (US)

( * ) Notice: Subject to any disclaimer, the term of this patent is extended or adjusted under 35 U.S.C. 154(b) by 181 days.

(21) Appl. No.: 13/005,511

(22) Filed: Jan. 12, 2011

(65) Prior Publication Data

US 2011/0212535 A1   Sep. 1, 2011

Related U.S. Application Data

(60) Provisional application No. 61/294,769, filed on Jan. 13, 2010.

(51) Int. Cl.
*G01N 25/18* (2006.01)

(52) U.S. Cl.
USPC ............ 436/149; 333/186; 333/197; 333/133

(58) Field of Classification Search .................. None
See application file for complete search history.

(56) References Cited

U.S. PATENT DOCUMENTS

| | | | |
|---|---|---|---|
| 5,501,893 A | 3/1996 | Laermer et al. |
| 6,437,445 B1 | 8/2002 | Lee et al. |
| 6,574,130 B2 | 6/2003 | Segal et al. |
| 6,643,165 B2 | 11/2003 | Segal et al. |
| 6,657,312 B2 | 12/2003 | Hirano |
| 6,682,677 B2 | 1/2004 | Lobovsky et al. |
| 6,706,402 B2 | 3/2004 | Rueckes et al. |
| 6,737,939 B2 | 5/2004 | Hoppe et al. |
| 6,759,693 B2 | 7/2004 | Vogeli et al. |
| 6,764,628 B2 | 7/2004 | Lobovsky et al. |
| 6,774,052 B2 | 8/2004 | Vogeli et al. |
| 6,784,028 B2 | 8/2004 | Rueckes et al. |
| 6,803,725 B2 | 10/2004 | Jin |
| 6,835,591 B2 | 12/2004 | Rueckes et al. |
| 6,836,424 B2 | 12/2004 | Segal et al. |
| 6,875,374 B1 | 4/2005 | Zhan et al. |
| 6,911,682 B2 | 6/2005 | Rueckes et al. |
| 6,919,592 B2 | 7/2005 | Segal et al. |
| 6,924,538 B2 | 8/2005 | Jaiprakash et al. |
| 6,942,921 B2 | 9/2005 | Rueckes et al. |
| 6,944,054 B2 | 9/2005 | Rueckes et al. |
| 6,979,590 B2 | 12/2005 | Rueckes et al. |
| 6,982,903 B2 | 1/2006 | Bertin et al. |
| 6,990,009 B2 | 1/2006 | Bertin et al. |
| 6,995,046 B2 | 2/2006 | Rueckes et al. |

(Continued)

OTHER PUBLICATIONS

Ahmed, S.K. et al., Effect of temperature on the electron field emission from aligned carbon nanofibers and multiwalled carbon nanotubes, *Applied Surface Science* 2007, vol. 254, pp. 610-615.

(Continued)

*Primary Examiner* — Robert Xu
(74) *Attorney, Agent, or Firm* — Steinfl & Bruno LLP

(57) ABSTRACT

Carbon nanofiber resonator devices, methods for use, and applications of said devices are disclosed. Carbon nanofiber resonator devices can be utilized in or as high Q resonators. Resonant frequency of these devices is a function of configuration of various conducting components within these devices. Such devices can find use, for example, in filtering and chemical detection.

22 Claims, 15 Drawing Sheets

U.S. PATENT DOCUMENTS

| | | |
|---|---|---|
| 7,045,421 B2 | 5/2006 | Rueckes et al. |
| 7,056,758 B2 | 6/2006 | Segal et al. |
| 7,071,023 B2 | 7/2006 | Bertin et al. |
| 7,075,141 B2 | 7/2006 | Rueckes et al. |
| 7,112,464 B2 | 9/2006 | Jaiprakash et al. |
| 7,112,493 B2 | 9/2006 | Bertin et al. |
| 7,113,426 B2 | 9/2006 | Rueckes et al. |
| 7,115,901 B2 | 10/2006 | Bertin et al. |
| 7,115,960 B2 | 10/2006 | Bertin et al. |
| 7,138,832 B2 | 11/2006 | Bertin et al. |
| 7,446,044 B2 | 11/2008 | Kaul |
| 2002/0113335 A1 | 8/2002 | Lobovsky et al. |
| 2003/0165074 A1 | 9/2003 | Segal et al. |
| 2003/0165648 A1 | 9/2003 | Lobovsky et al. |
| 2003/0234407 A1 | 12/2003 | Vogeli et al. |
| 2003/0236000 A1 | 12/2003 | Vogeli et al. |
| 2004/0009115 A1 | 1/2004 | Wee et al. |
| 2004/0075159 A1 | 4/2004 | Vogeli |
| 2004/0075379 A1 | 4/2004 | Jin |
| 2004/0077107 A1 | 4/2004 | Vogeli |
| 2004/0085805 A1 | 5/2004 | Segal et al. |
| 2004/0087162 A1 | 5/2004 | Voglei |
| 2004/0096389 A1 | 5/2004 | Lobovsky et al. |
| 2004/0108550 A1 | 6/2004 | Jin |
| 2004/0159833 A1 | 8/2004 | Rueckes et al. |
| 2004/0164289 A1 | 8/2004 | Rueckes et al. |
| 2004/0175856 A1 | 9/2004 | Jaiprakash et al. |
| 2004/0181630 A1 | 9/2004 | Jaiprakash et al. |
| 2004/0191978 A1 | 9/2004 | Rueckes et al. |
| 2004/0214366 A1 | 10/2004 | Segal et al. |
| 2004/0214367 A1 | 10/2004 | Segal et al. |
| 2004/0245209 A1 | 12/2004 | Jung et al. |
| 2005/0035344 A1 | 2/2005 | Bertin et al. |
| 2005/0035367 A1 | 2/2005 | Bertin et al. |
| 2005/0035786 A1 | 2/2005 | Bertin et al. |
| 2005/0035787 A1 | 2/2005 | Bertin et al. |
| 2005/0036365 A1 | 2/2005 | Bertin et al. |
| 2005/0037547 A1 | 2/2005 | Bertin et al. |
| 2005/0041465 A1 | 2/2005 | Rueckes et al. |
| 2005/0041466 A1 | 2/2005 | Rueckes et al. |
| 2005/0047244 A1 | 3/2005 | Rueckes et al. |
| 2005/0052894 A1 | 3/2005 | Segal et al. |
| 2005/0053525 A1 | 3/2005 | Segal et al. |
| 2005/0054128 A1 | 3/2005 | Gasparyan et al. |
| 2005/0056825 A1 | 3/2005 | Bertin et al. |
| 2005/0056866 A1 | 3/2005 | Bertin et al. |
| 2005/0056877 A1 | 3/2005 | Rueckes et al. |
| 2005/0058590 A1 | 3/2005 | Sen et al. |
| 2005/0058797 A1 | 3/2005 | Sen et al. |
| 2005/0058834 A1 | 3/2005 | Rueckes et al. |
| 2005/0059176 A1 | 3/2005 | Rueckes et al. |
| 2005/0059210 A1 | 3/2005 | Rueckes et al. |
| 2005/0062035 A1 | 3/2005 | Bertin et al. |
| 2005/0062062 A1 | 3/2005 | Bertin et al. |
| 2005/0062070 A1 | 3/2005 | Bertin et al. |
| 2005/0063210 A1 | 3/2005 | Segal et al. |
| 2005/0063244 A1 | 3/2005 | Bertin et al. |
| 2005/0065741 A1 | 3/2005 | Segal et al. |
| 2005/0067607 A1 | 3/2005 | Zhan et al. |
| 2005/0074569 A1 | 4/2005 | Lobovsky et al. |
| 2005/0074926 A1 | 4/2005 | Bertin et al. |
| 2005/0101112 A1 | 5/2005 | Rueckes et al. |
| 2005/0128788 A1 | 6/2005 | Segal et al. |
| 2005/0174842 A1 | 8/2005 | Bertin et al. |
| 2005/0191495 A1 | 9/2005 | Rueckes et al. |
| 2005/0237781 A1 | 10/2005 | Bertin et al. |
| 2005/0269553 A1 | 12/2005 | Sen et al. |
| 2005/0269554 A1 | 12/2005 | Sen et al. |
| 2005/0270824 A1 | 12/2005 | Bertin et al. |
| 2005/0279988 A1 | 12/2005 | Bertin |
| 2005/0280436 A1 | 12/2005 | Bertin |
| 2005/0281084 A1 | 12/2005 | Rueckes et al. |
| 2005/0282515 A1 | 12/2005 | Bertin |
| 2005/0282516 A1 | 12/2005 | Bertin |
| 2006/0044035 A1 | 3/2006 | Bertin |
| 2006/0061389 A1 | 3/2006 | Bertin |
| 2006/0125033 A1 | 6/2006 | Segal et al. |
| 2006/0128049 A1 | 6/2006 | Jaiprakash et al. |
| 2006/0183278 A1 | 8/2006 | Bertin et al. |
| 2006/0193093 A1 | 8/2006 | Bertin et al. |
| 2006/0204427 A1 | 9/2006 | Ghenclu et al. |
| 2006/0231865 A1 | 10/2006 | Rueckes et al. |
| 2006/0237857 A1 | 10/2006 | Bertin et al. |
| 2006/0250843 A1 | 11/2006 | Bertin et al. |
| 2006/0250856 A1 | 11/2006 | Bertin et al. |
| 2006/0255834 A1 | 11/2006 | Bertin |
| 2006/0276056 A1 | 12/2006 | Ward et al. |
| 2007/0254490 A1 | 11/2007 | Jain |

OTHER PUBLICATIONS

Bechtold, A. et al., Logic Circuits with Carbon Nanotube Transistors, *Science*, vol. 294, Nov. 9, 2001.

Chandrahalim, H., et al., High-k dielectrically transduced MEMS thickness shear mode resonators and tunable channel-select RF filters, *Sensors and Actuators A: Physical*, 2007, vol. 136, pp. 527-539.

Chen, I.C. et al., Extremely sharp carbon nanocone probes for atomic force microscopy imaging, Applied Physics Letters, 88, 2006.

Chhowalla, M. et al., Growth process conditions of vertically aligned carbon nanotubes using plasma enhanced chemical vapor deposition, Journal of Applied Physics, vol. 90, No. 10, Nov. 15, 2001.

Cruden, B.A. et al., Reactor design considerations in the hot filament/direct current plasma synthesis of carbon nanofibers, Journal of Applied Physics, vol. 94, No. 6, Sep. 15, 2003.

Dequesnes, M. et al., Calculation of pull-in voltages for carbon-nanotube-based nanoelectromechanical switches, *Nanotechnology* 2002, vol. 13, pp. 120-131.

Dujardin, E. et al., Self-assembled switches based on electroactuated multiwalled nanotubes, *Applied Physics Letters* 2005, vol. 87, pp. 193107-1-193107-3.

Eriksson, A. et al., Direct transmission detection of tunable mechanical resonance in an individual carbon nanofiber relay, *Nano Letters* 2008, vol. 8, pp. 1224-1228.

Fan, S. et al., Self-oriented regular arrays of carbon nanotubes and their field emission properties, *Science*, vol. 283, Jan. 22, 1999.

Helveg, S. et al., Atomic-scale imaging of carbon nanofibre growth, *Nature*, vol. 427, Jan. 29, 2004.

Hofmann, S. et al., Low-temperature growth of carbon nanotubes by plasma-enhanced chemical vapor deposition, *Applied Physics Letters*, vol. 83, No. 1, Jul. 7, 2003.

Huang, Z.P. et al., Growth of large periodic arrays of carbon nanotubes, *Applied Physics Letters*, Jan. 20, 2003, vol. 83, No. 3.

Husain, A. et al., Nanowire-based very-high frequency electromechanical resonator, *Applied Physics Letters*, 2003, vol. 83, pp. 1240-1242.

Ito, H., Dissolution behavior of chemically amplified resist polymers for 248-, 193-, and 157-nm lithography, *IBM J. RES & DEV*, vol. 45, No. 5, Sep. 2001.

Jackson, B.D. et al., Niobium titanium nitride-based superconductor-insulator-superconductor mixers for low-noise terahertz receivers, *Journal of Applied Physics* 2005, vol. 97, pp. 113904-1-113904-8.

Jang, J.E. et al., Nanoelectromechanical switches with vertically aligned carbon nanotubes, *Applied Physics Letters*, 2005, vol. 87, pp. 163114-1-163114-3.

Li, J. et al., Bottom-up approach for carbon nanotube interconnects, *Applied Physics Letter*, vol. 82, No. 15, Apr. 14, 2003.

Louchev, O.A. et al., Growth mechanism of carbon nanotubes forests by chemical vapor deposition, *Applied Physics Letters*, vol. 80, No. 15, Apr. 15, 2002.

Ng, H. et al., Growth of epitaxial nanowires at the junctions of nanowalls, *Science*, 2003, vol. 300, pp. 1249.

Nguyen, C., Frequency-Selective MEMS for Miniaturized Low-Power Communication Devices, *IEEE Trans. Microwave Theory and Techniques*, 1999, vol. 47, pp. 1486-1503.

Naik, A.K., et al., Towards single-molecule nanomechanical mass spectrometry, *Nature Nanotechnology*, 2009, vol. 4, pp. 445-450.

Ngo, Q. et al., Thermal interface properties of Cu-filled vertically aligned carbon nanofiber arrays, Nano Letters, vol. 4, Nov. 12, 2004.

Nolan, P.E. et al., Carbon deposition and hydrocarbon formation on group VIII metal catalysts, J. Phys. Chem. B, vol. 102, 1998.

Gaidarzhy, A., et al., Spectral response of a gigahertz-range nanomechanical oscillator, Appl. Phys. Lett., 2005, vol. 86, 254103.

Sazonova, V., et al., A tunable carbon nanotube electromechanical oscillator, Nature, 2004, vol. 431, pp. 284-287.

Peng, H.B., et al., Ultrahigh Frequency Nanotube Resonators, *Phys. Rev. Lett.*, 2006, vol. 97, 087203.

Poncharal, P., et al., Electrostatic Deflections and Electromechanical Resonances of Carbon Nanotubes, Science, 1999, vol. 283, pp. 1513-1516.

Comsol Multiphysics Version 3.4, Comsol AB, Tegnergatan 23, SE-111 40, Stockholm, Sweden. Found at the world wide website comsol.com. Website accessed Jan. 10, 2011.

Melechko, A. et al., Large-scale synthesis of arrays of high-aspect ratio rigid vertically aligned carbon nanofibres, *Nanotechnology*, 2003, vol. 14, pp. 1029-1035.

Melechko, A.V. et al., Vertically aligned carbon nanofibers and related structures: controlled synthesis and directed assembly, *Journal of Applied Physics*, 97, 2005.

Kaul, A.B. et al., In situ characterization of vertically oriented carbon nanofibers for three-dimensional nano-electro-mechanical device applications, *Nanotechnology*, 2010, vol. 21, 315501.

Kaul, A.B. et al., Electromechanical carbon nanotube switches for high frequency applications, *Nano Lett.*, 2006, vol. 6, No. 5, pp. 942-947.

Kaul, A. et al., Electrostatic switching in vertically oriented nanotubes for nonvolatile memory applications, *Material Resources Society Symposium Proceedings*, 2009, vol. 1186, pp. 1-6.

Kaul, A.B. et al., Interrogating vertically-oriented carbon nanofibers with nanomanipulation for nanoelectromechanical switching applications, *Applied Physics Letters*, 2009, vol. 95, 093103.

Ren Z. F. et al., Synthesis of large arrays of well-aligned carbon nanotubes of glass, *Science*, vol. 282, Nov. 6, 1998.

Rueckes, T. et al., Carbon nanotube-based nonvolatile random access memory for molecular computing, *Science*, 2000, vol. 289, pp. 94-97.

Saito, Y. et al., Emissions characteristics of niobium nitride field emitters, *Applied Surface Science*, 1999, vol. 146, pp. 177-181.

Shimoi, N. et al., Enhancement of electron field emission from carbon nanofiber bundles separately grown on Ni catalyst in Ni-Cr alloy, *Carbon*, 2009, vol. 47, pp. 1258-1263.

Siefert, F., et al., Mechanical sensors based on surface acoustic waves, *Sensors and Actuators A-Physical*, 1994, vol. 44 pp. 231-239.

Tachi, S. et al., Low-temperature reactive ion and microwave plasma etching of silicon, Applied Physic Letters, Feb. 22, 1988, vol. 52(8).

Teo, K.B.K. et al., Characterization of plasma-enhanced chemical vapor deposition carbon nanotubes by Auger electron spectroscopy, *Journal of Vacuum Science Technology B.*, 2002, vol. 20, pp. 116-121.

Teo, K.B.K. et al., Plasma enhanced chemical vapour deposition carbon nanotubes/nanofibers-how uniform do they grow?, Nanotechnology, 2003, vol. 14.

Yu, C. et al., Thermal contact resistance and thermal conductivity of a carbon nanofiber, ASME, vol. 128, Mar. 2006.

Zhang, Y. et al., Electric-field directed growth of aligned single-walled carbon nanotubes, Applied Physics Letters, vol. 79, No. 19, Nov. 5, 2001.

Zhang, X. et al., Guided neurite growth on patterned carbon nanotubes, Sensors and Actuators B, 106, 2005.

Notice of Allowance issued for U.S. Appl. No. 11/523,273, filed Sep. 19, 2006 in the name of Anupama B. Kaul et al., mail date: Jun. 17, 2008.

Notice of Allowance issued for U.S. Appl. No. 11/523,273, filed Sep. 19, 2006 in the name of Anupama B. Kaul et al., mail date: Jul. 23, 2008.

Examiner Interview Summary Record issued for U.S. Appl. No. 11/523,273 filed Sep. 19, 2006 in the name of Anupama B. Kaul et al., mail date: May 1, 2008.

Restriction Requirement issued for U.S. Appl. No. 12/694,235, filed Jan. 26, 2010 in the name of Anupama B. Kaul et al., mail date: Feb. 28, 2012.

International Technology Roadmap for Semiconductors, 2008 Update Overview: http://www.itrs.net/Links/2008/ITRS/Update/2008_Update.pdf.

Ominami, Y. et al., Structural Characteristics of Carbon Nanofibers for On-Chip Interconnect Applications, *Appl. Phys. Lett.*; 87, 233105 (2005).

Brinkmann, S. et al., Fundamental Differences in Mechanical Behavior between Two Types of Crystals at the Nanoscale, Phys. Rev. Lett., vol. 100, Issue 15, 155502 (2008), 4 pages; http://www.jrgreer.caltech.edu/.

Okuyama, H. et al., Position-Selective Growth of Vertically Aligned Carbon Nanotubes for Application of Electronic-Measuring Nanoprobes, *Physica E*; 37, 49-53 (2007).

Bumble, B. et al., Fabrication of Nb/Al-$N_x$/NbTiN Junctions for SIS Mixer Applications, *IEEE Trans. Appl. Supercond.*, vol. 11, 76-79 (2001).

Decade! Survey of the Solar System, 2003-2013 (http://www.lpi.usra.edu/opag/decadel_small.pdf).

Salvetat, J.P. et al., Mechanical Properties of Carbon Nanotubes, *Appl. Phys. A*; 69, 255-260 (1999).

Yu, M.F. et al., Strength and Breaking Mechanism of Multiwalled Carbon Nanotubes Under Tensile Load; *Science*, 287, 637 (2000).

Odom, T.W. et al., Atomic Structure and Electronic Properties of Single-Walled Carbon Molecules; *Nature* 391, 62-64 (1998).

Kim, P. et al., Nanotube Nanotweezers, *Science*, vol. 286, 2148-2150 (1999).

Collins, P.G. et al., Extreme Oxygen Sensitivity of Electronic Properties of Carbon Nanotubes, Science 287, 120 (2000).

Kinaret, J.M. et al, A Carbon-Nanotube-Based Nanorelay, *Appl. Phys. Lett.*, 82, 1287-1289 (2003).

Lee, S.W. et al., a Three-Terminal Carbon Nanorelay, *Nano Lett.*, vol. 4, 2027-2030 (2004).

Lee, S.W. et al, Production of Individual Suspended Single-Walled Carbon Nanotubes using the AC Electrophoresis Technique, *Appl. Phys. A* 78, 283-286 (2004).

Cha, S.N. et al., Fabrication of a Nanoelectromechanical Switch using a Suspended Carbon Nanotube, *Appl. Phys. Lett.*, vol. 86, 083105 (2005).

Tombler, T. et al., Reversible Electromechanical Characteristics of Carbon Nanotubes Under Local-Probe Manipulation, *Nature*, vol. 405, 769-772 (2000).

Minot, E.D. et al., Tuning Carbon Nanotube Band Gaps with Strain, *Phys. Rev. Lett.*, vol. 90, 156401 (2003).

Walters, D.A. et al., Elastic Strain of Freely Suspended Single-Wall Carbon Nanotube Ropes, *Appl. Phys. Lett.*, vol. 74, 3803-3805 (1999).

Franklin, N.R. et al., Integration of Suspended Carbon Nanotube Arrays into Electric Devices and Electromechanical Systems, *Appl. Phys. Lett.*, vol. 81, 913-915 (2002).

Wong, E.W. et al., Submicron Patterning of Iron Nanoparticle Monolayers for Carbon Nanotube Growth, *Chem. Mater.* 17, 237-241 (2005).

Manohara, H.M. et al., Carbon Nanotube Schottky Diodes Using Ti-Schottky and Pt-Ohmic Contacts for High Frequency Applications, *Nano Lett.*, vol. 5, 1469-1474 (2005).

Peroulis, D. et al., Electromechanical Considerations in Developing Low-Voltage RF MEMS Switches, *IEEE Trans. on Microwave Theory and Tech.*, vol. 51, 259-270 (2003).

Jonsson, L.M. et al., Effects of Surface Forces and Phonon Dissipation in a Three-terminal Nanorelay, *J. Appl. Phys.*, vol. 96, 629-635 (2004).

Duffy, S. et al., MEMS Microswitches for Reconfigurable Microwave Circuitry, *IEEE Microwave Wireless Comp. Lett.*, vol. 11, 106-108 (2001).

Rebeiz, G.M. et al., RF MEMS Switches and Switch Circuits, *IEEE Microwave Mag.* 2, 59-71 (2001).

Burke, P.J., An RF Circuit Model for Carbon Nanotubes, IEEE Trans. On Nanotech., vol. 2, 55-58 (2003).

Kaul, A.B. et al., Carbon nanotube vacuum gauges with wide dynamic range, *IEEE Trans. Nanotech.* 2009, vol. 8, pp. 252-257.

Kaul, A.B. et al., Single, aligned carbon nanotubes in 3D nanoscale architectures enabled by top-down and bottom-up manufacturable processes, *Nanotech.* 2009, 20, 075303.

Kaul, A.B., Gas sensing with long, diffusively contacted single-walled carbon nanotubes, *Nanotech.*, 2009, 20, 155501.

Non-Final Office Action issued for U.S. Appl. No. 12/694,235, filed Jan. 26, 2010 in the name of Anupama B. Kaul et al.; mail date: Jul. 18, 2012.

APPLICATIONS AND METHODS OF OPERATING A THREE-DIMENSIONAL NANO-ELECTRO-MECHANICAL RESONATOR AND RELATED DEVICES

CROSS REFERENCE TO RELATED APPLICATIONS

The present application claims priority to U.S. Provisional Application No. 61/294,769 entitled "Carbon Nanofiber based High Frequency, High Q, Miniaturized Mechanical Resonators", filed on Jan. 13, 2010, which is incorporated herein by reference in its entirety. The present application may be related to U.S. Pat. No. 7,446,044 entitled "Carbon Nanotube Switches for Memory, RF Communications and Sensing Applications, and Methods of Making the Same", issued on Nov. 4, 2008, which claims priority to U.S. Provisional Application No. 60/718,585 entitled "Nanotube based RF Switch, Tunable Capacitor and ESD Sensor", filed on Sep. 19, 2005, and also claims priority to U.S. Provisional Application No. 60/797,735 entitled "Nanotube based RF Switch, Tunable Capacitor and ESD Sensor", filed on May 3, 2006, the disclosures of which are each incorporated herein by reference in their entirety. The present application may also be related to U.S. patent application Ser. No. 12/694,235 entitled "Nanotubes and Related Manufacturing Processes," filed on Jan. 26, 2010, which claims priority to U.S. Provisional Application No. 61/206,115 entitled "High Throughput Nano-Manufacturability for the Formation of Single, Vertically Aligned Carbon Nanotubes in 3D Nanoscale Architectures for Electronics and Sensing Applications", filed on Jan. 28, 2009, the disclosures of which are each incorporated herein by reference in their entirety. The present application may also be related to U.S. patent application Ser. No. 12/849,784 entitled "Nano-electro-mechanical Switches Using Three-Dimensional Sidewall-Conductive Carbon Nanofibers and Method for Making the Same", filed on Aug. 3, 2010, which claims priority to U.S. Provisional Application No. 61/240,602, entitled "Carbon Nanofibers Synthesized on Selective Substrates for Nonvolatile Memory and 3D Electronics Applications", filed on Sep. 8, 2009, the disclosures of which are each incorporated herein by reference in their entirety.

STATEMENT OF GOVERNMENT GRANT

The invention described herein was made in the performance of work under a NASA contract, and is subject to the provisions of Public Law 96-517 (35 USC 202) in which the Contractor has elected to retain title.

FIELD

The present disclosure relates to carbon nanotubes, carbon nanofibers and nanoscale devices. In particular, it relates to applications and methods of operating a three-dimensional nano-electro-mechanical resonator and related devices.

BACKGROUND

In electronic resonators based on Si integrated circuits, continued reduction in device dimensions results in resistive loss increase and thus Q value decrease. Hence, Q values of small dimension electronic resonators may be lower than desired for some applications. Such loss mechanisms for Q values are absent, on the other hand, for mechanical resonators such as bulk acoustic wave (BAW) and surface acoustic wave (SAW) resonators since size reduction in mechanical devices is more limited. Therefore, higher Q values for both BAW and SAW resonators are possible compared to their electronic counterparts (see reference 1, incorporated herein by reference in its entirety).

Mechanical resonators also tend to have higher radiation tolerance, a factor which can make them suitable for higher radiation applications such as satellite and space applications. However, both BAW and SAW resonators involve low resonant frequencies and are also physically large, which precludes their integration into miniaturized electronic systems.

SUMMARY

According to a first aspect, a method of operating a nano-electro-mechanical resonator is provided, comprising: providing the nano-electro-mechanical resonator, wherein the nano-electro-mechanical resonator comprises: a first electrical conductor; and a second electrical conductor comprising at least one carbon nanofiber; applying a voltage signal containing an alternating current component between the first and the second electrical conductor; and producing mechanical resonance on the second electrical conductor via the voltage signal, thus operating the nano-electro-mechanical resonator.

According to a second aspect, a method of operating a nano-electro-mechanical resonator as a chemical detector is provided, comprising: providing a nano-electro-mechanical resonator, wherein the nano-electro-mechanical resonator comprises: a first electrical conductor; and a second electrical conductor comprising at least one carbon nanofiber with a functionalized layer suitable for binding to at least one selected type of chemical species, wherein the at least one selected type of chemical species is in a chemical-containing fluid; applying a voltage signal containing an alternating current component between the first and the second electrical conductor; producing a first mechanical resonance on the second electrical conductor by the voltage signal; contacting the chemical-containing fluid with the nano-electro-mechanical resonator such that the at least one selected type of chemical species binds to the functionalized layer of the second electrical conductor; producing a second mechanical resonance on the second electrical conductor, wherein the second mechanical resonance is different from the first mechanical resonance; and detecting the at least one selected type of chemical species in the chemical-containing fluid to the functionalized layer of the second electrical conductor, wherein the detecting comprises binding of the at least one selected type of chemical species to the functionalized layer and changing mass of the second electrical conductor, and wherein the changing mass produces the second mechanical resonance.

According to a third aspect, a nano-electro-mechanical resonator is provided, comprising: a first electrical conductor; and a second electrical conductor comprising at least one carbon nanofiber, the second electrical conductor positioned at a gap width from the first electrical conductor and positioned at a coupling length with the first electrical conductor, wherein the first and the second electrical conductor are configured to electro-mechanically couple when a voltage signal containing an alternating current component is applied between the first and the second electrical conductor, and wherein a first mechanical resonance is produced on the second electrical conductor, thus forming a nano-electro-mechanical resonator.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 9 shows an exemplary frequency filter.

DETAILED DESCRIPTION

Figure 1A:
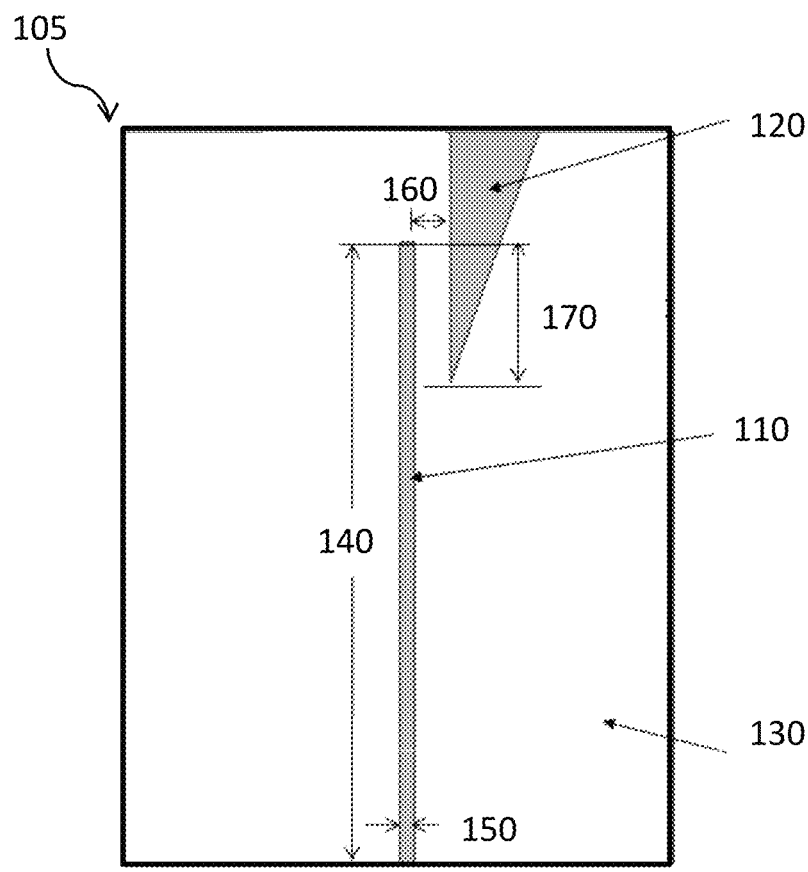
FIG. 1A shows a cross-sectional view of an exemplary three-dimensional (3D) nano-electro-mechanical resonator (NEMR).

To address issues such as low Q value generally associated with electronic resonators as well as low resonant frequency and large size generally associated with mechanical resonators, new materials and technologies, especially those which target high frequency regimes, such as the Gigahertz (GHz) range, are intensively being investigated. Generally speaking, desirable materials and technologies may have characteristics of high frequency operation, low power consumption, and small size.

In this regard, micro-electro-mechanical (MEM) resonator technologies have been addressing the issues by utilizing microscale feature sizes formed using conventional micromachining technology (see references 2 and 3, incorporated herein by reference in their entirety). Nanoscale structures, such as carbon nanofibers, have the potential to increase resonant frequencies and Q values even further due to their higher aspect ratios and inherently higher elastic modulus when compared to Si or metallic structures typically used in MEM resonators. Such nanoscale structures can be used in applications that involve any of high force constants, high responsivity, improved sensitivity, tunability, low loss (high Q), low power consumption, and small size.

Nanoscale resonators based on nano-electro-mechanical structures have recently been demonstrated using top-down, lithographically fabricated approaches to form cantilever or bridge-type structures (see references 4 and 5, incorporated herein by reference in their entirety). Top-down approaches generally involve complicated and expensive e-beam lithography as well as a release mechanism.

Resonance effects in structures synthesized using bottom-up approaches have also recently been reported. For example, single-walled carbon nanotubes or multi-walled carbon nanotubes, where the nanotubes were laterally suspended across a trench, have been driven into resonance using a mixing technique with the substrate acting as a gate electrode (see references 6 and 7, incorporated herein by reference in their entirety). In earlier reports, resonance effects have been observed in multi-walled carbon nanotubes that were randomly oriented out of the plane of the substrate (see reference 8, incorporated herein by reference in its entirety).

In what follows, applications and methods of operating a three-dimensional nano-electro-mechanical resonator and related devices are described in accordance with various embodiments of the present disclosure. Specifically, Applicants describe resonance in single, vertically aligned carbon nanofibers fabricated using a bottom-up approach, where the vertical orientation of the carbon nanofibers and the three-dimensional configuration have the potential to increase integration density even further for system-level applications.

Applicants' AC modeling analysis utilizes COMSOL Multiphysics, which is a commercially available finite element simulator (see reference 9, incorporated herein by reference in its entirety). Further, Applicants describe in-situ observation, conducted using a scanning-electron-microscope (SEM), of mechanical resonances in individual carbon nanotubes.

The term "carbon nanofiber(s)" can be used interchangeably with "carbon nanotube(s)" and "carbon nanowire(s)". The term "carbon nanofiber(s)" or CNF(s) is defined herein as any fiber, tube or wire made of primarily carbon and has nanoscale diameter (also referred to as width). Specifically the diameter of the CNF can be between 8 nm and 500 nm. Length of the CNF can be few nanometers to several microns long or longer.

Also for clarity purposes, the term "nano-electro-mechanical resonator" or NEMR refers herein to a three-dimensional nano-electro-mechanical resonator comprising at least one CNF. The NEMR is described in the present disclosure in various embodiments with a single carbon nanofiber, but can be fabricated and operated with multiple carbon nanofibers in bundles or arrays. The NEMR may comprise nanofibers made from materials such as silicon or germanium.

Carbon nanotubes typically have an elongated cylindrical form with respect to its diameter and are generally hollow. CNFs are also elongated and cylindrical in form with high aspect ratio and may be hollow or solid depending on synthesis conditions. Transmission-electron-micrographs (TEM) of the CNFs of the present disclosure indicate that graphene layers are inclined to the central axis with a cone angle of 25 degrees as shown in reference 11 (incorporated herein by reference in its entirety).

Figure 12A:
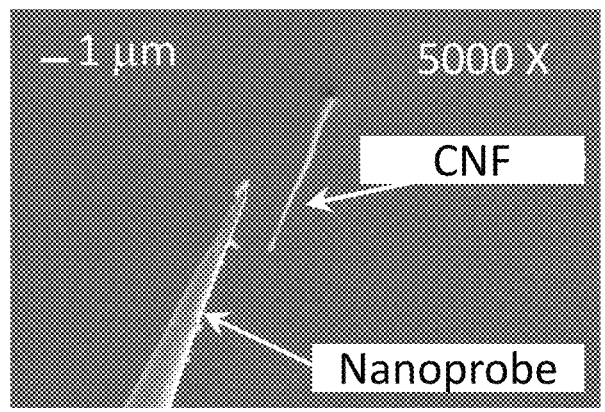
FIG. 12A shows a scanning electron microscope picture of an exemplary NEMR comprising a CNF and a nanoprobe.
Figure 12B:
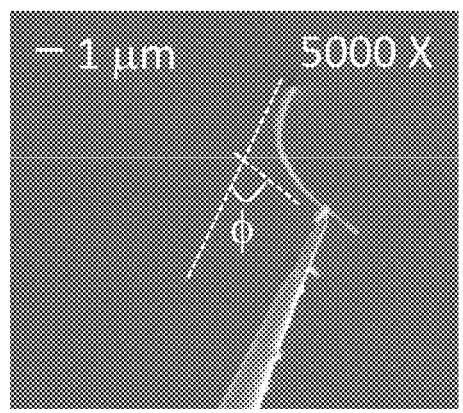
FIG. 12B shows a scanning electron microscope picture of an exemplary NEMR comprising a CNF and a nanoprobe, where the nanoprobe bends the CNF but does not cause any visible delamination or fracturing.
Figure 12C:
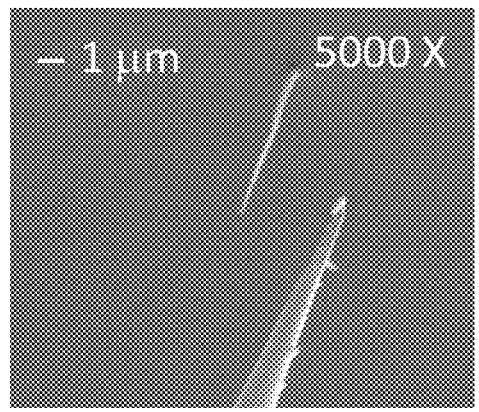
FIG. 12C shows a scanning electron microscope picture of an exemplary NEMR comprising a CNF and a nanoprobe, where the CNF returns elastically to its initial straight position with no visible fracturing or delamination.

The CNFs of the present disclosure can be well adhered to the substrate, as shown in FIGS. 12A, 12B, and 12C. A nanoprobe is used to mechanically deflect a single CNF and cause bending of the CNF. The CNF undergoes bending angles φ as large as 70 degrees (see FIG. 12B) and returns elastically to its initial position (see FIG. 12C) without delaminating from the substrate and without fracturing the CNF body. Multiple bending cycles have been observed, and the result suggests the CNFs of the present disclosure are robust and suited for resonator applications, where it would undergo a large number of vibrations during operation.

FIG. 1A shows a cross-sectional view of a nano-electro-mechanical resonator (NEMR) (105), according to one embodiment of the present disclosure, comprising a CNF (110) and a nanoprobe (120), where both the CNF (110) and the nanoprobe (120) are surrounded by a solution (130). Other embodiments of the present disclosure may use a second CNF (not shown) or a metal rod (not shown) or other conducting materials in place of the nanoprobe (120). In the embodiment with one CNF, the CNF (110) is positioned with a gap width (160) and a coupling length (170) to the nanoprobe (120) as indicated in FIG. 1A, and can be on a substrate (not shown in FIG. 1A). The CNF (110) has a diameter (150) and a length (140).

Figure 1B:
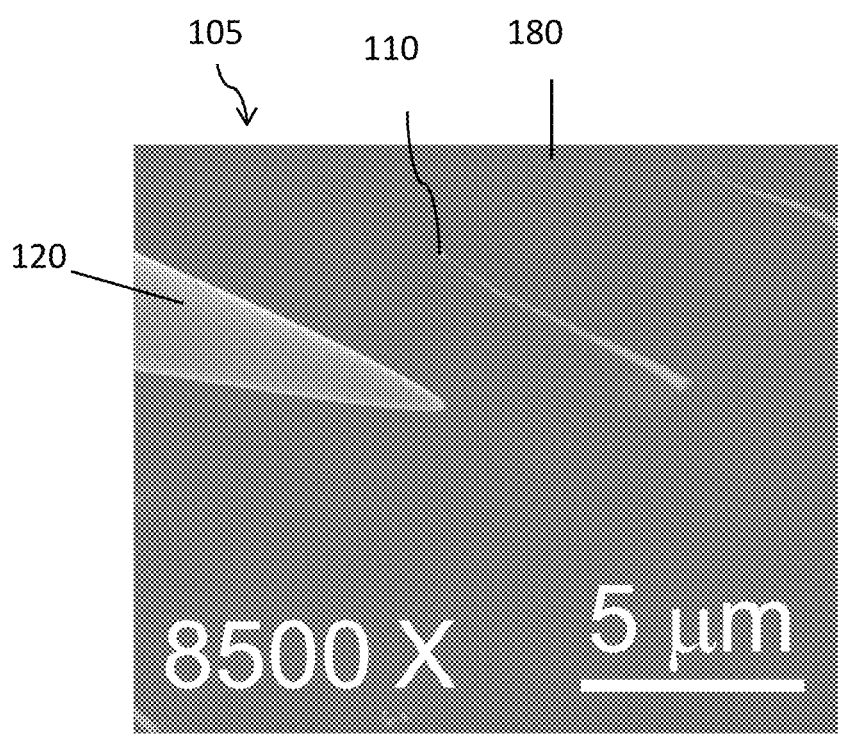
FIG. 1B shows a scanning electron microscope picture of an exemplary 3D NEMR.

FIG. 1B shows an SEM image of an NEMR (105) comprising a vertically aligned CNF (110) synthesized at nominal growth conditions (discussed in the next paragraph) on a Si substrate (180). The SEM image was taken on a sample mounted on a 45° beveled holder. The NEMR (105) also comprises a nanoprobe (120).

According to an embodiment of the present disclosure, with continued reference to FIG. 1B, the CNF (110) can be fabricated on a Si wafer substrate (180) with pre-patterned Ni catalyst islands (not shown) in a plasma-enhanced chemical vapor deposition (PECVD) growth system. By way of example and not of limitation, high purity acetylene ($C_2H_2$) and ammonia ($NH_3$) can be introduced at 700° C., which can serve as the carbon feedstock and diluent gas, respectively, to the PECVD system. In some embodiments, DC discharge of the PECVD system can be ignited at a power of around 200 W and growth can be carried out for a fixed duration when the desired growth pressure has been attained (around 5 Torr). The CNF (110) may be substantially perpendicular to the substrate (180). More details regarding fabrication techniques can be found in cross-referenced U.S. patent application Ser. No. 12/694,235 for "Nanotubes and Related Manufacturing Processes," filed on Jan. 26, 2010.

The CNF (110) may or may not have conductive sidewalls. The substrate (180) may or may not be covered by additional layers, such as niobium titanium nitride (NbTiN) or silicon dioxide ($SiO_2$). Whereas cross-referenced U.S. patent application Ser. No. 12/849,784 for "Nano-electro-mechanical Switches Using Three-Dimensional Sidewall-Conductive Carbon Nanofibers and Method for Making the Same," filed on Aug. 3, 2010, discloses conductive sidewalls and substrates for some applications with direct current (DC) input voltage, the NEMR of the present disclosure is not limited to conductive sidewalls and substrates.

In accordance with a further embodiment of the disclosure and with continued reference to FIG. 1B, the nanoprobe (120) can be made of tungsten and can be used to make in-situ measurements on the CNF (110) on the substrate (180) mounted on a nanomanipulator nanoprobe stage inside an SEM. The solution (130 of FIG. 1A) surrounding the NEMR (105) can be vacuum or a fluid. The nanoprobe (120) can be used to make one of the two terminal contacts of the CNF (110), where the substrate (180) can serve as the other terminal (usually ground). The person skilled in the art will understand that such an experimental technique (fabrication and measurement method) is exemplary and others can be provided and utilized.

Referring to FIG. 1A and in one embodiment of the disclosure, simulations of a vertically oriented CNF (110) can be performed using COMSOL Multiphysics. The simulations can be performed in a two-dimensional (2D) geometry to minimize computational complexity. By way of example and not of limitation, the CNF (110) can be assumed to have a uniform density ρ of around 1.5 g/cm³, elastic modulus $E_b$ of around 600 GPa, relative permittivity $\in_r$ of around 5.0, and Poisson's ratio ν of around 0.2. Although the relative permittivity and Poisson's ratio may not be known accurately, a sensitivity analysis in COMSOL can show that the resonant frequency does not depend strongly on these parameters. The solution (130) which surrounds the NEMR (105) is assumed to be a vacuum in the simulations.

With continued reference to FIG. 1A, structural strain and deflection of the CNF (110) can be obtained from the simulations from electrostatic interaction between the CNF (110) and the nanoprobe (120) in proximity to the CNF (110). In the simulation, the CNF resonator (110) tip and body are not spatially constrained, while all other surfaces are physically fixed at a position (including the CNF (110) base which can be fixed on a substrate (not shown in FIG. 1A)).

In one embodiment of the disclosure, the simulation conditions are mechanically analogous to a fixed cantilevered beam adjacent to the nanoprobe (120), where the nanoprobe (120) can be assumed to have infinite stiffness and infinite thickness. By way of example and not of limitation, electrostatic boundary conditions can be chosen such that the CNF (110) is electrically grounded and an alternating current (AC) voltage is applied to the nanoprobe (120). In addition, all other boundaries and surfaces can be assumed to have zero net electrical charge in FIG. 1A.

Figure 2:
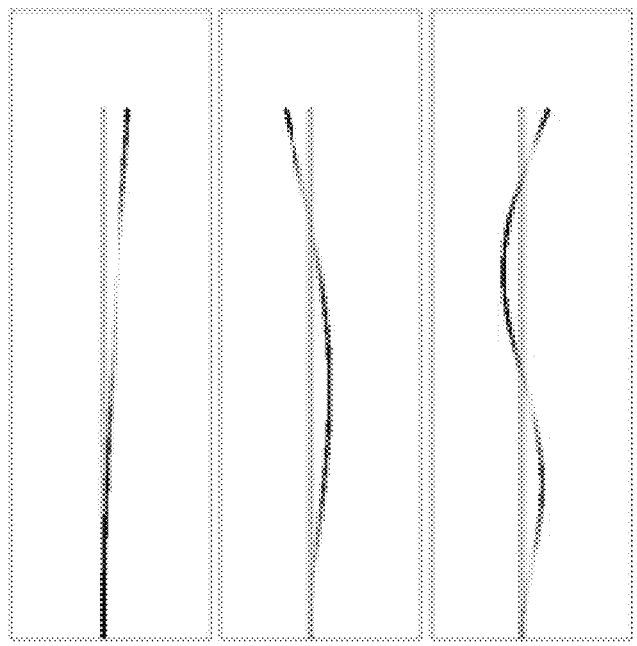
FIG. 2 shows an exemplary carbon nanofiber (CNF) of a 3D NEMR at resonance. Specifically, first three harmonic modes of resonance for the exemplary CNF are shown.

In a further embodiment of the disclosure, the resonant frequencies of the CNF (110) of the NEMR (105) in FIG. 1A can be derived from vibration analysis (see reference 10, incorporated herein by reference in its entirety) using an analytical calculation to determine the harmonic modes (also known as eigenmodes) of resonance of the CNF (110) via COMSOL Multiphysics and by using a model of the AC voltage developed in COMSOL. FIG. 2 shows deflection of the CNF resonator (110 in FIG. 1A) for each of the first three harmonic modes of resonance, where the results agreed with those expected qualitatively from classical vibration analysis.

In an exemplary embodiment, the AC voltage applied to the nanoprobe (120) of FIG. 1A includes an additional direct current (DC) component ($V_{Dc} \ll 1$ V), which facilitates faster convergence of the simulation solution than the AC voltage without the DC component. The DC component of the voltage signal attracts the CNF (110) to the nanoprobe (120) due to an attractive electrostatic force and thus causes greater coupling, which aids in the convergence of the simulation solution. The exemplary embodiment utilizes the AC voltage applied to the nanoprobe (120) with a DC component and utilizes the frequency response of the CNF (110) to monitor the amplitude of deflection, phase, and capacitance of the CNF (110).

Analytical Model and Comparison to COMSOL

Vibration analysis (see reference 10) allows the Applicants to develop an expression for the resonant modes of a cantilevered beam. In the case of a CNF (110) and with continued reference to FIG. 1A, the resonant frequency of the $j^{th}$ harmonic is described by Equation (1) as follows (see reference 8), $$f_j = \frac{\beta_j^2}{8\pi L^2}\sqrt{D_o^2 + D_i^2}\sqrt{\frac{E_b}{\rho}}, j = 1, 2, 3, \ldots \quad (1)$$

where L is the CNF length (140), $E_b$ (also denoted simply as E) is the elastic modulus of the CNF (110), and $\rho$ is the density of the CNF (110). Outer (150) and inner diameters of the CNF are denoted by $D_o$ and $D_i$ respectively, and $\beta_j$ is a constant for the $j^{th}$ harmonic $\omega_j$, where $\beta_1=1.875$, $\beta_2=4.694$, $\beta_3=7.855$, such that:

$$\omega_1 = 1.875^2\sqrt{\frac{EI}{mL^4}}, \omega_2 = 4.694^2\sqrt{\frac{EI}{mL^4}}, \omega_3 = 7.855^2\sqrt{\frac{EI}{mL^4}},$$

as taken from reference 10. Here E, I, m and L are the elastic modulus, moment of inertia, mass and length of a cantilevered beam, respectively. The Bernoulli-Euler analysis for a cantilevered elastic beam yields the solution shown in Equation (1). For the CNF grown using plasma-enhanced chemical vapor deposition (PECVD), it was assumed that the inner diameter $D_i$ is nearly 0 nm, since PECVD synthesized CNFs are generally not hollow (although increase in the hydrogen ratio during growth causes the cone angle to increase and thus can increase the potential for hollow CNFs).

Figure 3A:
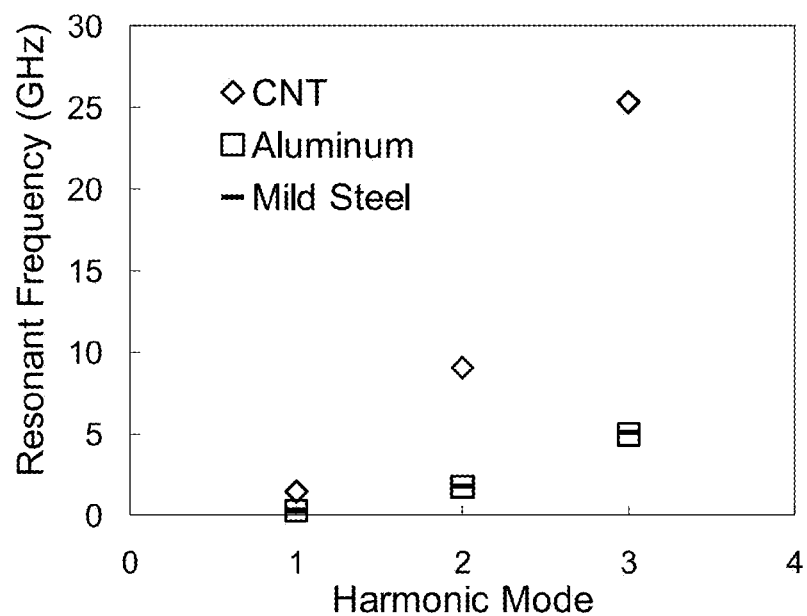
FIG. 3A shows a plot of resonant frequency for the first three harmonic modes of an exemplary CNF, and compares the resonant frequencies to those of nanofibers made of conventional materials such as aluminum and steel.

The Applicants determine the first three harmonic modes of resonance for a CNF using Equation (1) (assuming $E_b$ of around 1 TPa). Measurements of elastic modulus on the CNFs reveal values close to 0.9 TPa (reference 10). The first three harmonic modes of resonance are also calculated for aluminum and mild steel, both of which have a lower elastic modulus than carbon, and shown in FIG. 3A. FIG. 3A shows that, for high elastic modulus CNF, resonant frequencies in the hundreds of MHz to tens of GHz are possible. FIG. 3A also shows that the resonant frequency of the CNF is around five times larger than that determined when using other materials.

Figure 3B:
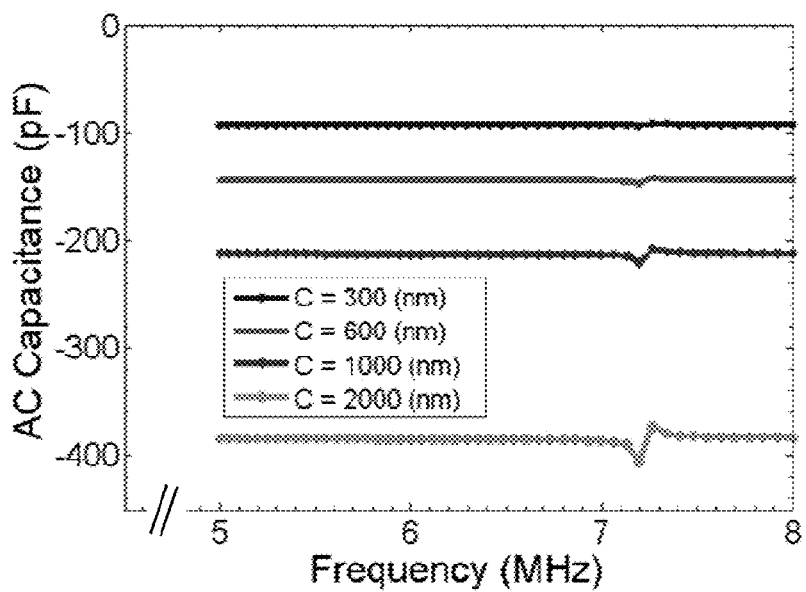
FIG. 3B shows a plot of alternating current (AC) capacitance as a function of frequency for an exemplary NEMR at various coupling lengths.

Referring back to FIG. 1A, dependence of the CNF resonant frequency and AC capacitance are also examined as a function of coupling length (170) between the nanoprobe (120) and the CNF (110) of the NEMR (105). As shown in FIG. 3B, the AC capacitance tended to increase with coupling length (170), indicated as "C" in FIG. 3B. Consequently, capacitance can be scaled by adjusting the coupling length (170), as a standard parallel plate capacitor model would suggest.

Phase and AC Capacitance

Figure 4A:
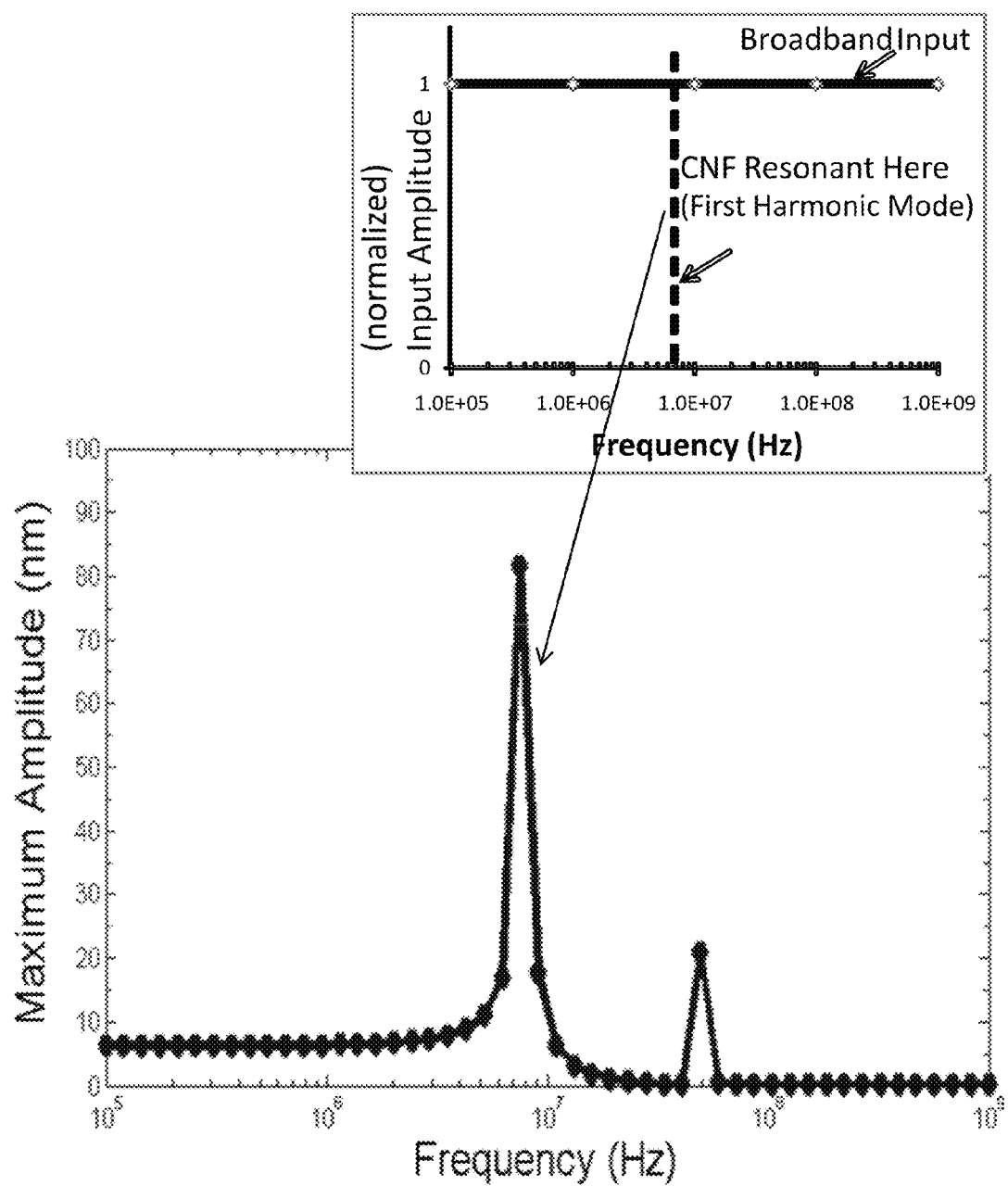
FIG. 4A shows amplitude of mechanical deflection for a CNF at its first harmonic mode of resonance in an exemplary NEMR as a function of frequency of an applied AC signal.

FIG. 4A shows the frequency dependence of the CNF tip deflection, where a peak is seen at resonance. The inset shows that a broadband AC signal is present at the input. Specifically, FIG. 4A shows that when an applied AC signal below the first harmonic is applied to the nanoprobe, a small mechanical deflection at the tip of the CNF can be observed. At the first harmonic mode of resonance, the amplitude of tip deflection peaks.

In contrast, tip deflection corresponding to the second harmonic (also shown in FIG. 4A) and higher harmonics (not shown) is smaller relative to that of the first harmonic mode. It should be noted that for a broadband AC signal on the nanoprobe, maximal deflection in the CNF occurred only when the frequency of the incoming signal is near or equal to the mechanical resonant frequency of the CNF in the NEMR. Since the CNF is significantly coupling to an AC signal when the frequency of the AC signal is near or equal to the mechanical resonant frequency of the CNF and insignificantly coupling at other frequencies, such frequency dependence can be useful for frequency filtering applications such as in communications systems.

Figure 4B:
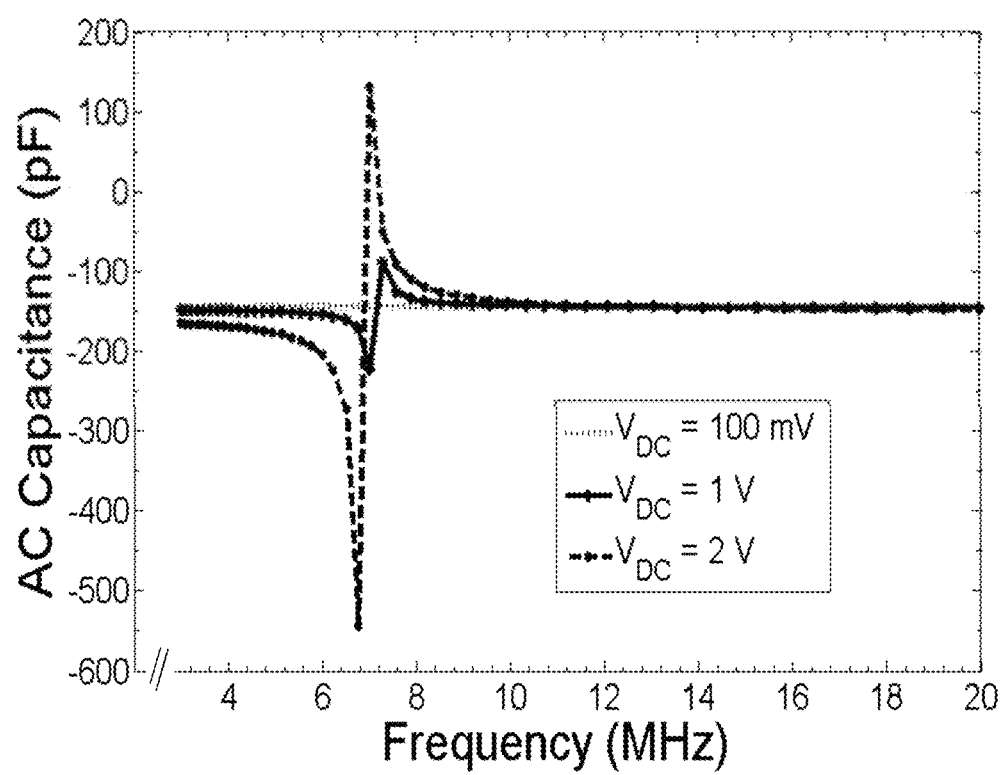
FIG. 4B shows the AC capacitance of an exemplary simulated NEMR with a CNF of nominal geometry for various DC bias solutions.

FIG. 4B shows the AC capacitance of the CNF as a function of a DC bias solution, where the AC signal has an amplitude $V_{AC}=1$ V. Simulations of the AC capacitance of the system shows that for DC biases of less than around 100 mV, no change in AC capacitance is found. For $V_{DC}>100$ mV, the AC capacitance of the CNF changes significantly near the first harmonic mode of resonance and approaches an asymptotic limit at the first harmonic mode of resonance, but is approximately constant above and below the frequency attributed to the first harmonic mode of resonance. It is assumed that for small DC bias solutions ($V_{DC}+|V_{AC}|<V_{PI}$, where $V_{PI}$ is the pull-in voltage, the voltage at which the nanoprobe will cause the CNF to pull in and stay in contact with the nanoprobe), the shape of the CNF resonator's frequency response does not change.

With continued reference to FIG. 4B, the AC capacitance of a simulated NEMR with a CNF of nominal geometry for various DC bias solutions suggests that DC bias behaves as a gating voltage in controlling the onset of AC capacitance change at the frequency corresponding to a harmonic mode of resonance. Consequently, the resonance behavior of the CNF enabled by the AC capacitance change can be turned ON and OFF by adjusting the DC bias (shown as $V_{DC}$ in FIG. 4B). The data shows that a DC bias greater than a gating voltage, which is the case for $V_{DC}=1$ V, allows the CNF to demonstrate AC capacitance involved in resonance, while a DC bias smaller than a gating voltage, which is the case for $V_{DC}=100$ mV, does not cause the CNF to show AC capacitance change at the resonant frequency. This dependence of the AC capacitance on the DC bias may be a result of charge accumulating on the CNF surface.

Figure 5:
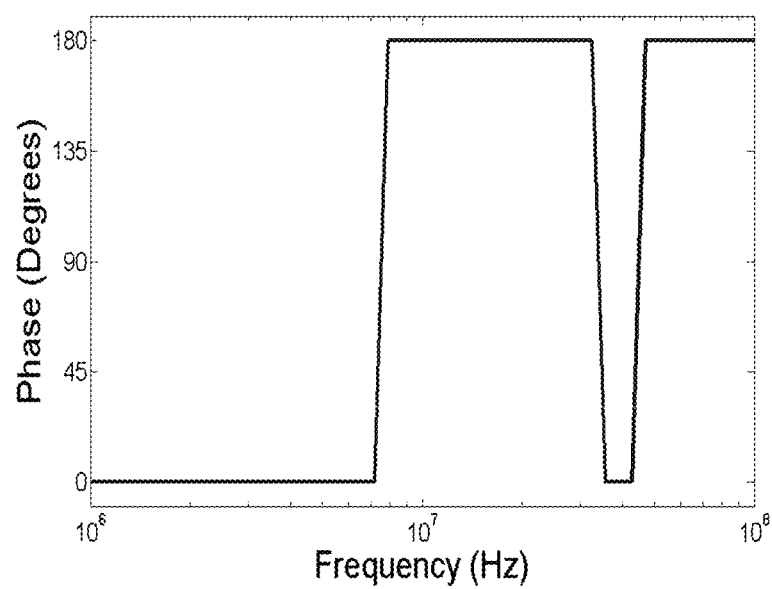
FIG. 5 shows phase difference between an electro-mechanical resonance signal of the NEMR and the AC component of the applied voltage signal at the input.

FIG. 5 shows phase difference between an electro-mechanical resonance signal of the CNF tip of the NEMR and the AC component of the voltage signal applied to the nanoprobe (120) of FIG. 1A. At the first harmonic frequency of resonance (around $7.7 \times 10^6$ Hz), the phase of the electro-mechanical resonance signal at the CNF tip shifts by 180° with respect to the applied signal. Consequently, this phase shift could serve as an indicator of resonance in various physical applications.

Resonance Dependence on Geometry

Figure 6A:
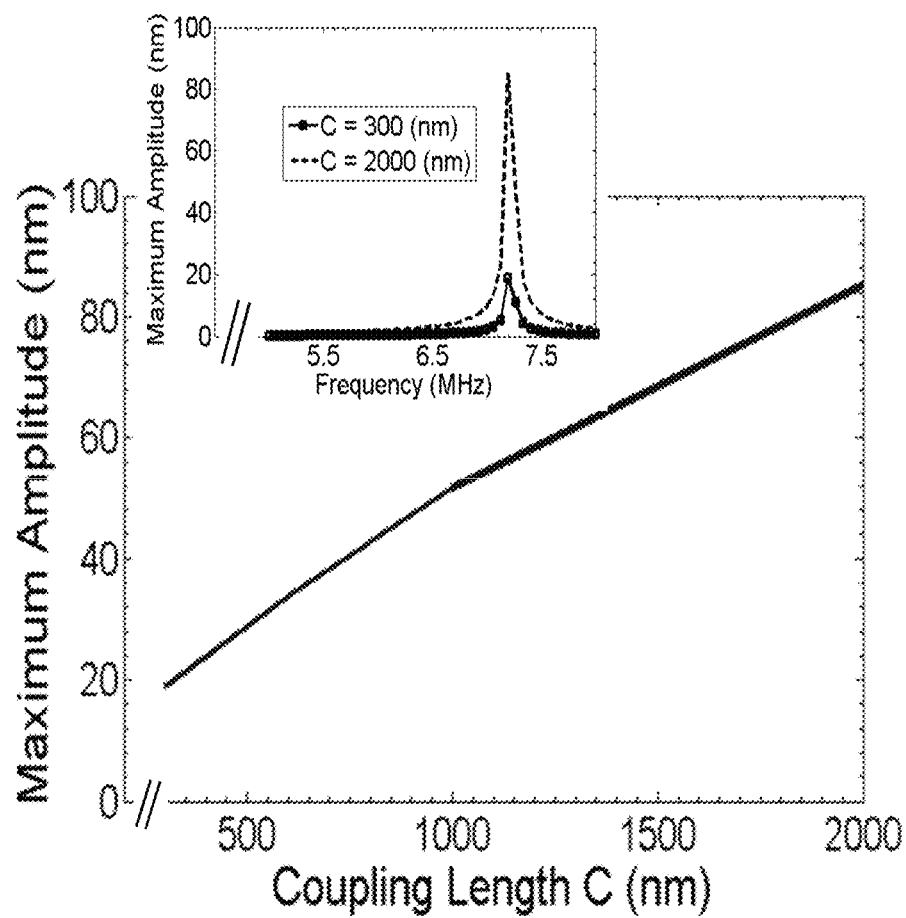
FIG. 6A shows the vibration amplitude of an exemplary simulated NEMR as a function of coupling length.

Referring back to FIG. 1A, the coupling length (170) and the gap width (160) can be varied experimentally via use of a nanomanipulator probe stage. Therefore, COMSOL simulations are conducted to investigate the impact of the coupling length (170) and the gap width (160) on the behavior of the NEMR (105) comprising a CNF (110). The dependence of the CNF vibration amplitude as a function of the coupling length (170) is shown in FIG. 6A with coupling length (170) indicated as "C". FIG. 6A shows that as coupling length (170) increases, the vibration amplitude also increases linearly. FIG. 6A also shows that a minimum coupling length is required for the NEMR to exhibit significant vibrational amplitude in resonance.

The inset shows the amplitude as a function of the frequency for two separate coupling lengths (170 of FIG. 1A). It should be noted that the Q value is higher for the larger coupling length of 2000 nm than the smaller coupling length of 300 nm.

Figure 6B:
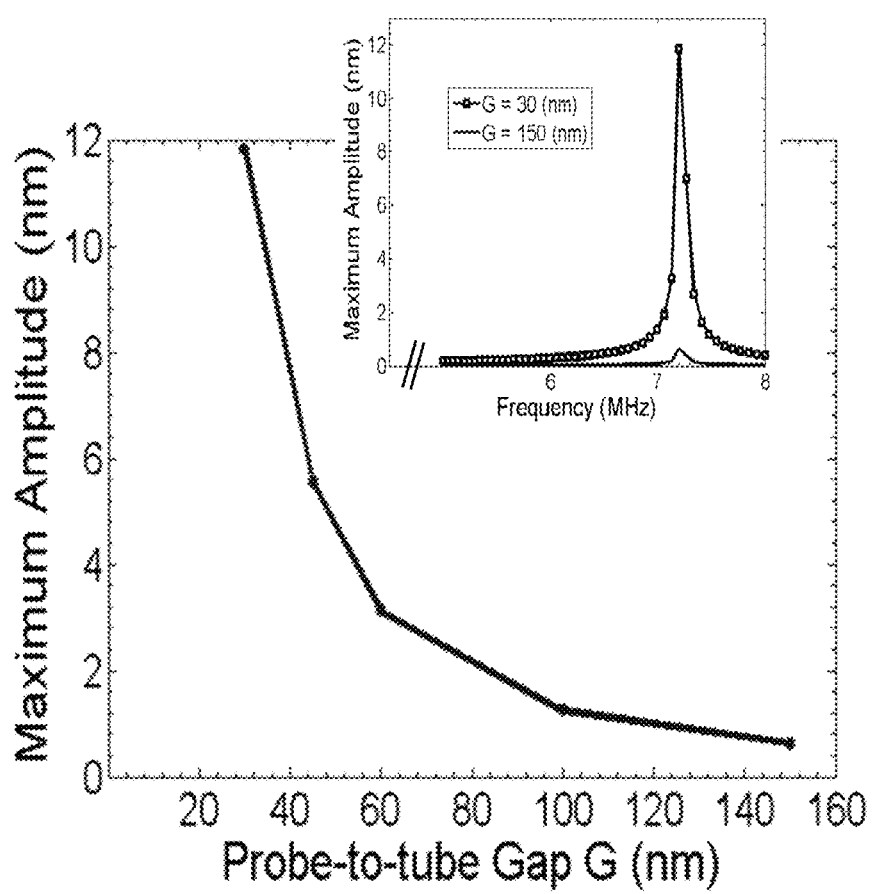
FIG. 6B shows the vibration amplitude of an exemplary simulated NEMR as a function of gap width.

FIG. 6B shows the vibration amplitude as a function of gap width (160 of FIG. 1A). FIG. 6B indicates that as the nanoprobe (120 of FIG. 1A) is moved further away from the CNF (110 of FIG. 1A) as shown with increasing gap width (160 of FIG. 1A), the vibration amplitude decreases. Gap width is referred to as probe-to-tube gap or "G" in FIG. 6B. Specifically, FIG. 6B shows a $1/G^2$ trend between G and the deflection amplitude. The inset in FIG. 6B indicates that the amplitude is maximal at the resonant frequency and that the smaller gap width, G, of around 30 nm yields a higher Q than the larger gap width G of around 150 nm.

In-Situ Observations of Resonance

Figure 7A:
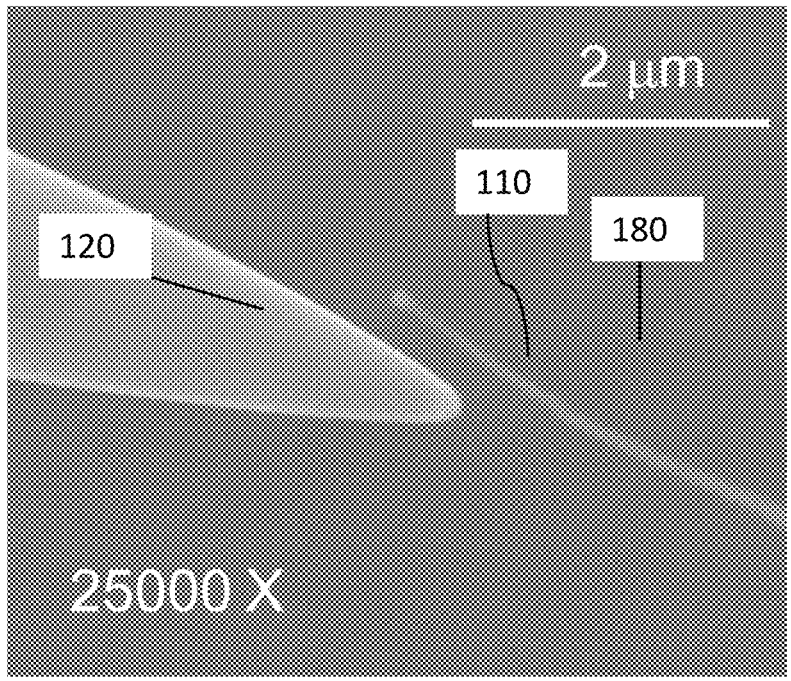
FIG. 7A shows a scanning electron microscope picture of an exemplary NEMR at a gap width greater than a threshold gap width. In this case, no mechanical resonance is observed.

In one embodiment of the present disclosure, as shown in FIG. 7A, at a gap distance larger than a threshold gap distance between the CNF (110) and the nanoprobe (120), there is no observed mechanical vibration indicating resonance although the CNF is not perfectly straight along its body, as the low magnification image in FIG. 7A also indicates.

Figure 7B:
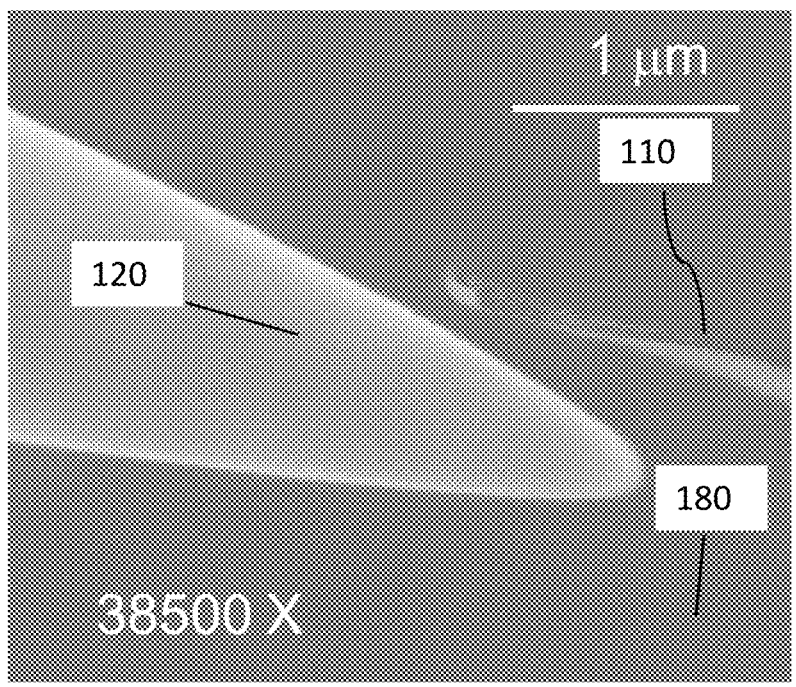
FIG. 7B shows a scanning electron microscope picture of an exemplary NEMR at a gap width smaller than the threshold gap width. In this case, mechanical resonance is observed in the CNF.
Figure 8:
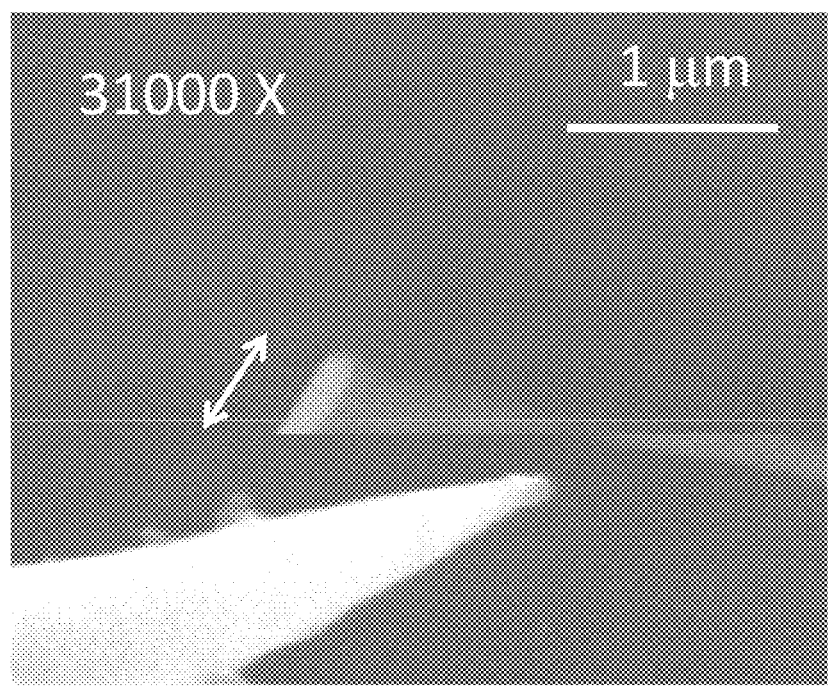
FIG. 8 shows a scanning electron microscope picture of an exemplary NEMR at a gap width smaller than the threshold gap width. In this case, mechanical resonance with large amplitude equivalent to several times the diameter of the CNF is observed.

FIG. 7B shows the nanoprobe (120) as it is brought into proximity to the CNF (110). Mechanical vibrations are induced in the CNF (110). FIG. 8 shows larger amplitude deflections in the CNF (110), where the deflections are several times larger in magnitude than the diameter of the CNF (110). These in-situ observations of resonance in individual, vertically oriented tubes confirm the simulation trends obtained using COMSOL Multiphysics concerning gap width as shown in FIG. 6B. Specifically, a gap width smaller than a threshold gap width is required for significant mechanical vibration of the CNF at resonance for the NEMR. In general, the results suggest that vertically oriented CNFs can be used in forming high Q, high frequency NEMRs with a smaller footprint due to the CNFs' three-dimensional architecture, which increases integration density by 10-100×.

EXAMPLES

Figure 9:
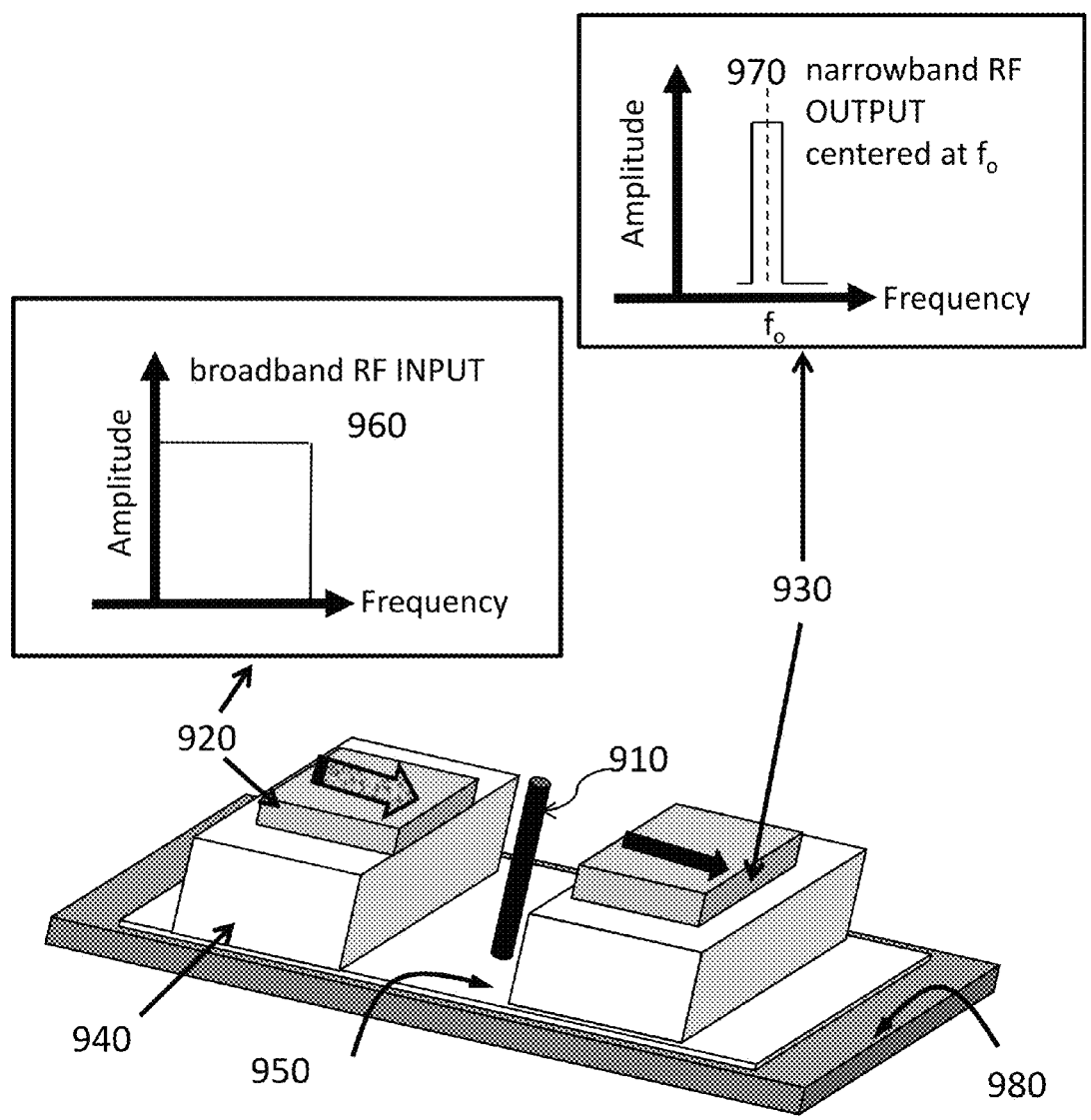
FIG. 9 shows a perspective view of a schematic of an exemplary NEMR configured as a frequency filter. A broadband input signal to and the narrowband output signal of the frequency filter are also shown.

FIG. 9 shows a perspective view of a schematic of an NEMR configured as a frequency filter. The NEMR comprises a CNF (910), an input conductive microstrip line (920), an output conductive microstrip line (930), a dielectric layer (940), a metal layer (950) and a silicon substrate (980). The metal layer (950) can be used to ground the CNF (910) while the dielectric layer (940) serves to insulate the input conductive microstrip line (920) and the output conductive microstrip line (930) from the metal layer (950). A broadband RF signal (960) can be directed to the CNF (910) by the input conductive microstrip line (920). As shown by the simulation results in FIG. 4A, only the resonant frequency in a broadband input signal will be coupled to the CNF (910). The mechanical resonance of the CNF (910) can be coupled to the output conductive microstrip line (930) and produce a narrowband RF signal output (970) at the resonant frequency shown as $f_o$ in FIG. 9.

Figure 10:
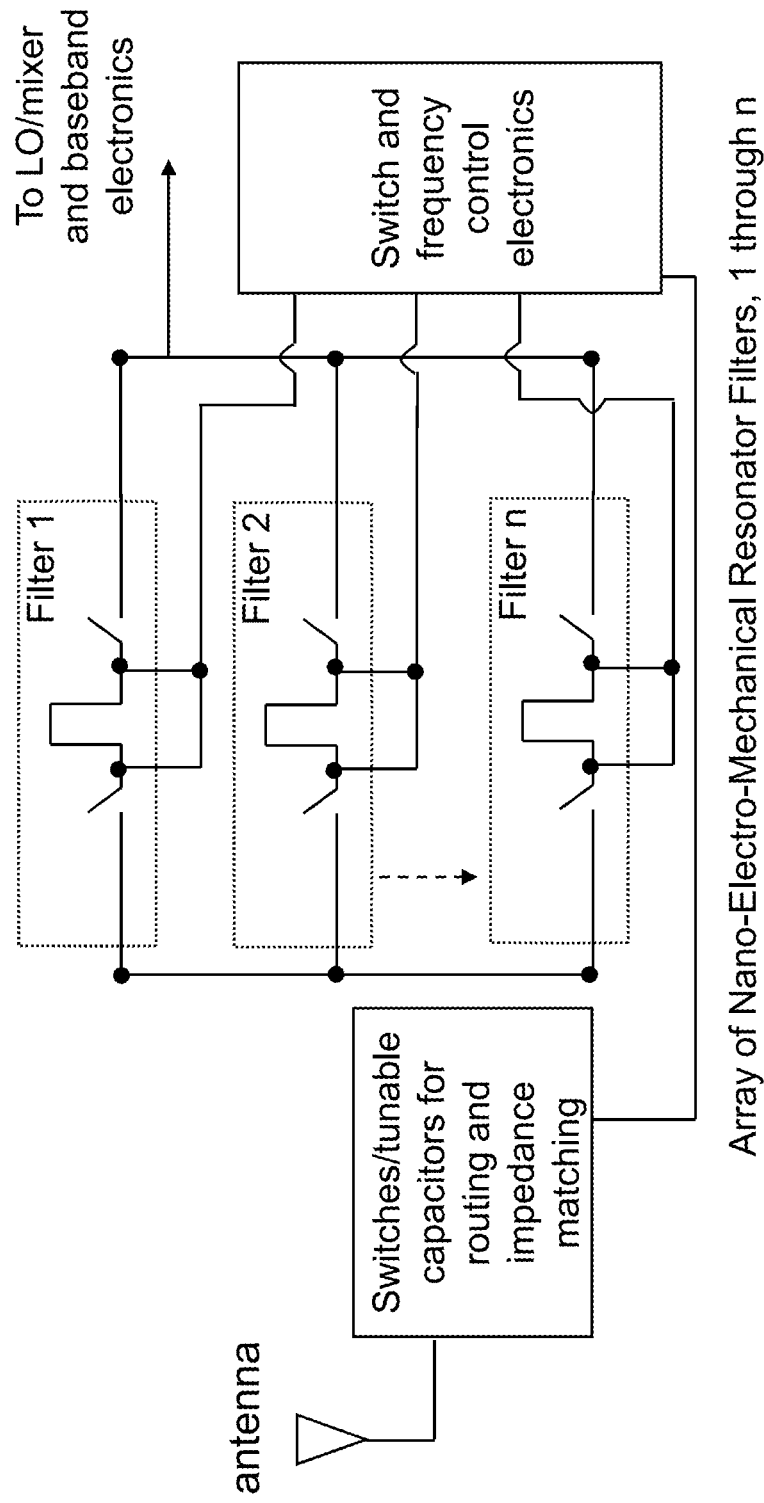
FIG. 10 shows a schematic of an exemplary frequency filter system made by a series of n frequency filters, where

FIG. 10 shows a schematic of a frequency filter system made by a series of n frequency filters, where FIG. 9 shows an exemplary frequency filter. The NEMR frequency filters can be used in the RF front-end of a transceiver for routing and transmitting data at a wide bandwidth (spanning frequencies of filter 1 through filter n). Resonant frequency of each NEMR can be tuned based on selecting the length and diameter of the CNF. The diameter of the CNF can be reduced by decreasing the thickness of the catalyst used. Also the type of catalyst used will determine in certain cases whether a CNT or CNF results during PECVD synthesis. In the case of Ni catalyst, CNFs are typically formed. In the case of Co/Ti catalyst, the probability of forming multi-walled carbon nanotubes (MWCNTs) or double-walled carbon nanotubes (DWCNTs) is increased. Besides length and diameter, the resonant frequency can also be impacted by the mass or degree of hollowness present in the nanotubes which will differ in the case of MWCNT, DWCNTs or CNFs, and their related surface characteristics. The resonant frequency possible for CNFs and carbon nanotubes (e.g., MWCNTs and DWCNTs) allow for a highly integrated, ultra-low power, high data rate, and wide bandwidth NEMR based transceiver architecture.

It is noted that the hydrogen gas ratio can be changed to result in a hollow CNF with a catalyst such as Ni. By using a thin Ni film (around 2-5 nm), one can generate hollow CNFs with thinner diameter. An alternate catalyst system such as Co/Ti can also be utilized to increase the likelihood to yield hollow CNFs (MWCNT or DWCNTs) with the PECVD synthesis technique in order to tune resonant frequency. Hollow CNFs can have different spring constant to mass ratio, resulting in different resonant frequency, compared to non-hollow CNFs.

Figure 11:
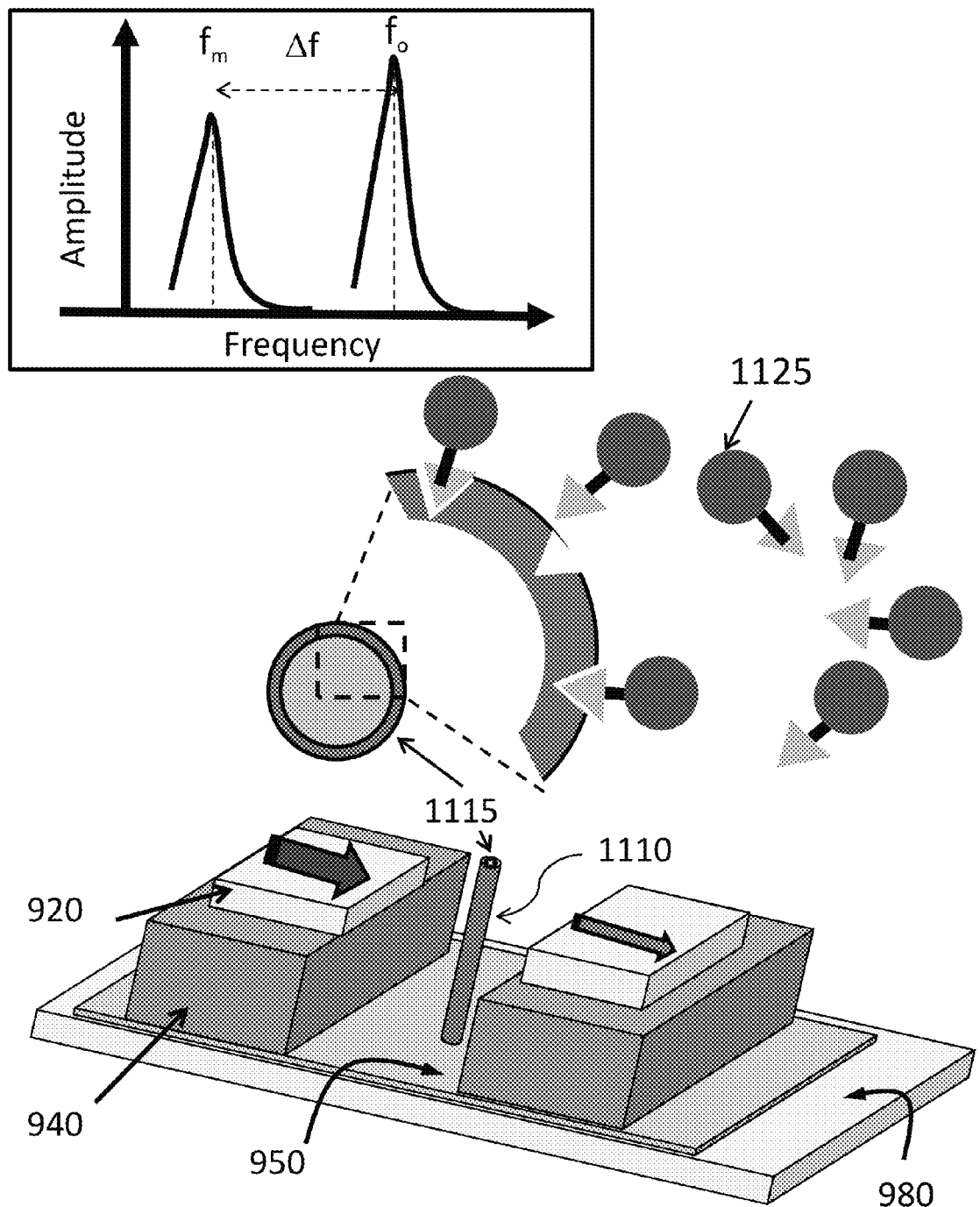
FIG. 11 shows a perspective view of a schematic of an exemplary nano-electro-mechanical chemical detector utilizing an NEMR. A graph showing resonant frequencies of the functionalized CNF, before and after target species binding, is also provided.

FIG. 11 shows a perspective view of yet another possible application of the NEMR as a nano-electro-mechanical chemical detector (NEMCD), and also shows a resonant frequency graph. Just as in FIG. 9, the NEMCD comprises an input conductive microstrip line (920), an output conductive microstrip line (930), a dielectric layer (940), a metal layer (950) and a silicon substrate (980). The CNF (1110) of the NEMCD, however, comprises a functionalized layer (1115) that surrounds the CNF (1110) and provides binding sites for one or more selected or targeted chemical species (1125) or molecules as shown in the upper inset in FIG. 11.

When a chemical-containing fluid is introduced to the NEMCD, the fluid being a vapor or liquid, the selected chemical species (1125) will selectively bind to the surface of the CNF (1110) and the mass increase of the CNF (1110) will shift the resonant frequency lower. Thus, the chemical species (1125) can be detected, and the concentration of the chemical species (1125) can be quantified by measuring change in resonant frequency.

The initial, pre-binding resonant frequency ($f_o$) and the post-binding resonant frequency ($f_m$) as shown in FIG. 11 can be measured, utilizing capacitive sensing, by mechanical-electrical coupling between the CNF (1110) and the output conductive microstrip line (930) as previously described in FIG. 9.

Figure 13:
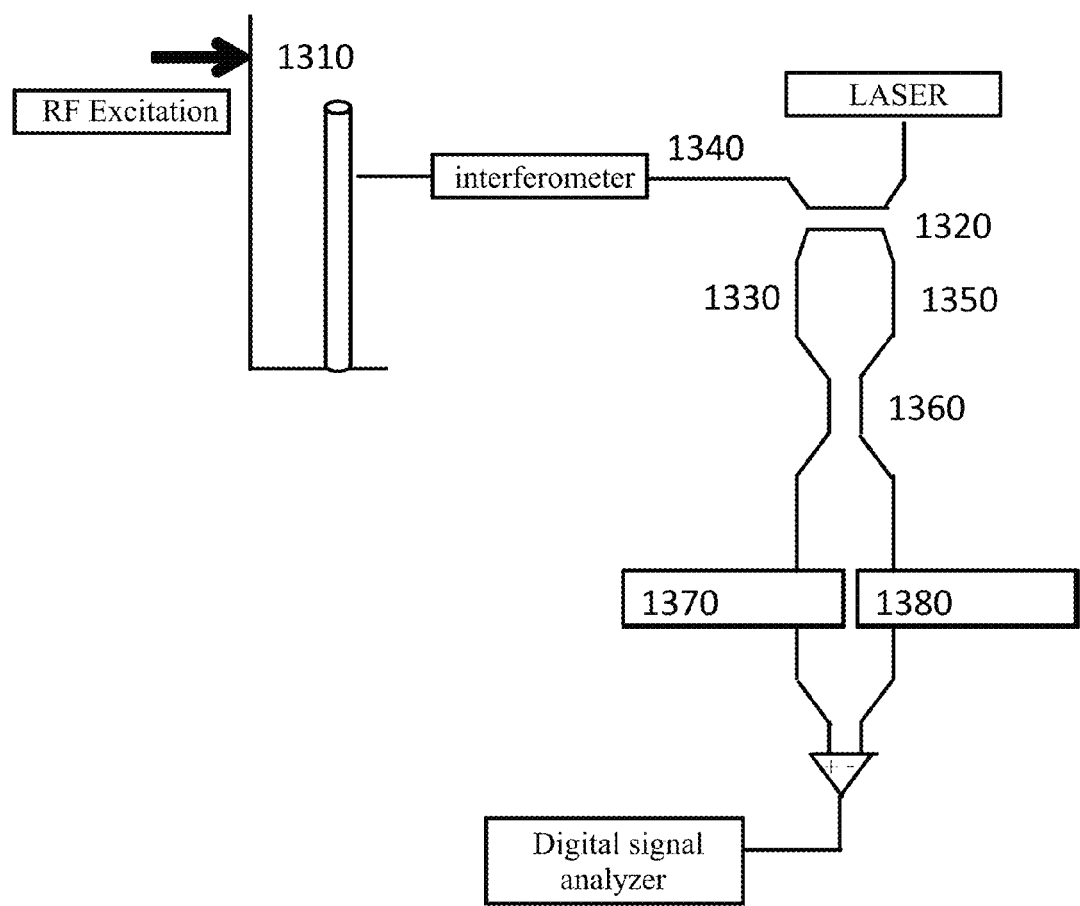
FIG. 13 shows a schematic of an exemplary optical system for reading the resonance of an NEMR.

The NEMCD and other NEMR can also utilize other forms of inputs and outputs in its integration into microscale and nanoscale circuits. For example, the input and output can have opto-electrical components. FIG. 13 shows that an exemplary embodiment where the mechanical resonance of the NEMR can be optically detected utilizing laser interference sensing of the deflection to convert the mechanical signal into an optical signal that can be measured by an optical detector and used in an optical circuit.

FIG. 13 shows light from a laser beam emitted into one branch of a first directional coupler (1320). The first directional coupler (1320) divides the laser beam into a reference beam (1330) and a measurement beam (1340). The light reflected from a vibrating CNF (1310) surface is coupled back into the fiber and divided by the first directional coupler (1320) to result in an output beam (1350). This output beam (1350) is then mixed with the reference beam (1330) at a second directional coupler (1360). As the CNF (1310) vibrates, it causes the path length of the output beam (1350) to vary. This variation of the path length causes modulation in the light intensity at the output, which is then monitored by a first photodetector (1370) and a second photodetector (1380). A differential output from the photodetectors (1370 & 1380) can be monitored using a digital signal analyzer.

The examples set forth above are provided to give those of ordinary skill in the art a complete disclosure and description of how to make and use the embodiments of the present disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. For example, the person skilled in the art will understand that the number steps or components shown is only indicative and that the method can occur in more or fewer steps and that the system may contain more or less components according to the various embodiments. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

LIST OF REFERENCES

1. F. Siefert, W. Bulst, and C. Ruppel, Sensors and Actuators A-Physical 44, 231(1994).
2. H. Chandrahalim, D. Weinstein, L. F. Cheow, and S. A. Bhave, Sensors and Actuators A: Physical 136, 527 (2007).
3. C. Nguyen, IEEE Trans. Microwave Theory and Techniques 47, 1486 (1999).
4. A. K. Naik, M. S. Hanay, W. K. Hiebert, X. L. Feng, M. L. Roukes, Nature Nanotechnology 4, 445 (2009).
5. A. Gaidarzhy, G. Zolfagharkhani, R. L. Badzey, and P. Mohanty, Appl. Phys. Lett. 86, 254103 (2005).
6. V. Sazonova, Y. Yaish, H. Ustunel, D. Roundy, T. A. Arias, and P. L. McEuen, Nature 431, 284 (2004).
7. H. B. Peng, C. W. Chang, S. Aloni, T. D. Yuzvinsky, and A. Zettl, Phys. Rev. Lett. 97, 087203 (2006).
8. P. Poncharal, Z. L. Wang, D. Ugarte, and W. A. de Heer, Science 283, 1513 (1999).
9. COMSOL Multiphysics Version 3.4, COMSOL AB, Tegnérgatan 23, SE-111 40, Stockholm, Sweden. Found at the worldwide website comsol.com. Website accessed Jan. 10, 2011.
10. L. Meirovich, *Elements of Vibration Analysis*, McGraw-Hill, New York, Second Edition (1986).
11. A. B. Kaul, K. G. Megerian, A. Jennings, and J. R. Greer, *Nanotechnology* 21, 315501 (2010).

The invention claimed is:

1. A method of operating a nano-electro-mechanical resonator, comprising:
    applying to a first structural member of the resonator, a voltage signal containing an alternating current (AC) component, the first structural member having a non-contacting proximity relationship with a second structural member, the second structural member comprising a carbon nanofiber, the non-contacting proximity relationship characterized at least in part by: a) a gap width separating the first structural member from the carbon nanofiber and b) a coupling length factor defined on the basis of a portion of the first structural member that is oriented substantially parallel to a portion of the carbon nanofiber; and
    producing mechanical resonance on the carbon nanofiber via the voltage signal, thus operating the nano-electro-mechanical resonator wherein the first structural member is one of: a) a nanoprobe, b) another carbon nanofiber or c) a metal rod.

2. The method according to claim 1, wherein the first structural member is a nanoprobe.

3. The method according to claim 1, wherein the voltage signal further contains a direct current bias higher than a gating voltage.

4. The method according to claim 1, wherein the carbon nanofiber comprises conductive sidewalls.

5. The method according to claim 1, wherein the gap width is less than a threshold gap width for producing mechanical resonance on the carbon nanofiber.

6. The method according to claim 1, wherein the coupling length is greater than a threshold coupling length for producing mechanical resonance on the carbon nanofiber.

7. The method according to claim 1, further comprising:
    selecting length, inner diameter, and outer diameter of the carbon nanofiber based on a target resonant frequency at which to operate the nano-electro-mechanical resonator.

8. The method according to claim 1, further comprising:
    generating an output voltage signal containing an output alternating current component on a third structural member by coupling the third structural member to the mechanical resonance on the carbon nanofiber.

9. The method of claim 8, wherein phase difference between the output alternating current component of the output voltage signal and the alternating current component of the input voltage signal is 180 degrees.

10. The method according to claim 1, further comprising generating an output optical signal based on the mechanical resonance on the carbon nanofiber.

11. The method according to claim 2, wherein the nanoprobe comprises tungsten.

12. The method according to claim 2, wherein the nanoprobe has a tapered portion.

13. The method according to claim 12, wherein the nanoprobe has a planar portion opposing the tapered portion, the planar portion configured to provide the gap width and coupling length factor with respect to the carbon nanofiber.

14. The method of claim 1, further comprising:
selecting the coupling length on the basis of a Q value, wherein the Q value is directly proportional to the coupling length.

15. The method of claim 1, further comprising:
selecting the gap width on the basis of a Q value, wherein the Q value is inversely proportional to the gap width.

16. The method of claim 15, wherein the mechanical resonance comprises a deflection amplitude, the deflection amplitude inversely proportional to the square of the gap width.

17. The method of claim 1, further comprising:
using the first structural member to mechanically deflect the carbon nanofiber.

18. The method of claim 17, wherein deflecting the carbon nanofiber comprises bending the carbon nanofiber to a first bending angle.

19. The method of claim 18, wherein the first bending angle is approximately 70 degrees.

20. The method of claim 19, wherein bending the carbon nanofiber to approximately 70 degrees is characterized by the carbon nanofiber returning to an initial position without delaminating from a substrate upon which the carbon nanofiber is anchored.

21. The method of claim 19, wherein bending the carbon nanofiber to approximately 70 degrees is characterized by the carbon nanofiber returning to an initial position without fracturing the carbon nanofiber.

22. The method of claim 18, further comprising:
bending the carbon nanofiber multiple times to test for robustness of the carbon nanofiber in producing mechanical resonance.

* * * * *